United States Patent
Strömberg et al.

(10) Patent No.: US 8,709,727 B2
(45) Date of Patent: Apr. 29, 2014

(54) MAGNETIC DETECTION OF SMALL ENTITIES

(76) Inventors: Mattias Strömberg, Uppsala (SE); Jenny Göransson, Uppsala (SE); Klas Gunnarsson, Uppsala (SE); Mats Nilsson, Bromma (SE); Peter Svedlindh, Uppsala (SE); Maria Strømme, Uppsala (SE)

( * ) Notice: Subject to any disclaimer, the term of this patent is extended or adjusted under 35 U.S.C. 154(b) by 638 days.

(21) Appl. No.: 12/678,171

(22) PCT Filed: Sep. 17, 2008

(86) PCT No.: PCT/IB2008/053789
§ 371 (c)(1),
(2), (4) Date: May 4, 2010

(87) PCT Pub. No.: WO2009/037659
PCT Pub. Date: Mar. 26, 2009

(65) Prior Publication Data
US 2011/0059444 A1  Mar. 10, 2011

Related U.S. Application Data

(60) Provisional application No. 60/972,918, filed on Sep. 17, 2007.

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search
None
See application file for complete search history.

(56) References Cited

U.S. PATENT DOCUMENTS

| 2002/0081714 A1* | 6/2002 | Jain et al. ................. 435/287.2 |
| 2004/0121364 A1* | 6/2004 | Chee et al. ...................... 435/6 |
| 2010/0009456 A1* | 1/2010 | Prins et al. ..................... 436/164 |

FOREIGN PATENT DOCUMENTS

WO  2007/092941 A1  8/2007

OTHER PUBLICATIONS

Jarvis et al, Nature Methods, 3:725-727 (Sep. 2006).
Schweitzer et al, Proceedings of the National Academy of Sciences of USA, 97(18):10113-10119 (2000).
Stromberg et al, Journal of Physics D. Applied Physics, 40(5):1320-1330 (Feb. 16, 2007).
Stoeva et al, Journal of the American Chemical Society, 127(44):15362-15363.
Connolly et al, Journal of Magnetism and Magnetic Materials, 225(1-2):156-160 (2001).
Sun et al, Surface and Coatings Technology, 201(1-2):250-254 (Sep. 12, 2006).
Fannin et al, Journal of Physics E. Scientific Instruments, 19(3):238-239 (1986).
Soderberg et al, Nature Methods, 3(12):995-1000 (Dec. 2006).
Landegren et al, Comparative and functional Genomics, 4:525-530 (2003).
Jaffrezic-Renault et al, Sensors, 7:589-614 (Apr. 30, 2007).
Stromberg et al, Biosensors & Bioelectronics, 24(4):696-703 (Dec. 1, 2008).

* cited by examiner

*Primary Examiner* — Kenneth R. Horlick
*Assistant Examiner* — David Thomas
(74) *Attorney, Agent, or Firm* — Porter Wright Morris & Arthur LLP

(57) ABSTRACT

A novel detection or quantifying method for biological entities or molecules such as, but not limited to, DNA, microorganisms and pathogens, proteins and antibodies, that by themselves are target molecules or from which target molecules are extracted, comprises the steps of i) forming target molecule-dependent volume-amplified entities, ii) allowing magnetic nanoparticles to bind to said volume-amplified entities, and iii) measuring changes in dynamic magnetic response of the magnetic nanoparticles caused by the increase in hydrodynamic volume of said magnetic nanoparticles.

21 Claims, 6 Drawing Sheets

MAGNETIC DETECTION OF SMALL ENTITIES

RELATED APPLICATIONS

The present application is a 371 of PCT/IB2008/053789 filed Sep. 17, 2008 and claims priority under 35 U.S.C. §119 of U.S. Application Ser. No. 60/972,918 filed Sep. 17, 2007.

FIELD OF THE INVENTION

The present invention relates to a novel detection or quantifying method for biological entities or molecules such as, but not limited to, DNA, microorganisms and pathogens, proteins and antibodies, that by themselves are target molecules or from which target molecules are extracted. The methods comprise the steps of i) forming target molecule-dependent volume-amplified entities, ii) allowing magnetic nanoparticles to bind to said volume-amplified entities, and iii) measuring changes in dynamic magnetic response of the magnetic nanoparticles caused by the increase in hydrodynamic volume of said magnetic nanoparticles or measuring the magnetic field due to the magnetic nanoparticles as they bind to a sensor surface functionalized with a secondary capturing probe.

The present invention further relates to biosensors and kits to be used in such a method.

BACKGROUND OF THE INVENTION

There is a need for novel simple assay formats for sensitive DNA sequence analyses as well as for detection of RNA and proteins, suitable for e.g. a clinical setting, bed-side applications, military purposes, forensic analyses, food and pharmaceutical product analyses, as well as analyses of microorganisms in the environment.

Below, the state of the art of DNA sequence analysis is briefly recapitulated.

Information about the presence and/or nature of DNA sequences is of importance in many areas such as e.g. in clinical diagnostics, to guide therapy and make accurate diagnosis of disease and in analysis of microorganisms present in the environment. Recently, immunoassay techniques have emerged that use DNA as reporter molecules to indicate detection of specific protein analytes, making DNA analysis techniques useful for all biomolecules of interest for diagnosis (IMMUNO-PCR [Sano et al.], IMMUNO-RCA [Schweitzer et al.], Bio-barcodes [Nam et al.], PLA [Fredriksson et al.]). DNA sequence detection schemes often rely on a hybridization reaction between a target-DNA molecule and a probe molecule, designed to match the target. Large-scale DNA hybridization analyses are efficiently performed using high-density microarrays of synthetic oligonucleotide probes and optical readout using e.g. fluorescence labelling and fluorescence detection, quantum dot labelling and metal colloid labels taking advantage of surface plasmon scattering phenomena [Bally et al.]. Microarray analysis is relatively labour-some and time-consuming, and limited in sensitivity and specificity, and is therefore not very suitable for diagnostics. It is an advantage if hybridizations can be monitored in homogenous readout formats that do not require separation of unbound labelled probes from the matching probe-target complexes. One commonly used technique to achieve this is based on detection of the change in fluorescence depolarization when a probe binds its target. Other readout formats for hybridization reactions, more suitable for diagnostics, have been explored. These involve e.g. electrochemical detection schemes [Kerman et al.], where monitoring of the hybridization reaction is based on the electrochemical response when the probes, labelled with e.g. organic dyes, metal complexes and metal nanoparticles, bind their targets. There also exist gravimetric detection schemes such as micro-cantilever resonance-based DNA detection with nanoparticle probes [Su et al.]. To achieve high detection sensitivity—in the extreme case single molecule detection—it is typically necessary to amplify the probe-target complex. One of the most commonly used methods for this is the polymerase chain reaction (PCR) [Saiki et al.]. Although the PCR scheme in principle provides unlimited sensitivity and quantitative dynamic range, the technique is considered too complicated for the diagnostic setting.

An alternative approach for enzymatic detection and amplification for detecting sets of gene sequences with high specificity and selectivity involves the use of circularizing oligonucleotide probes (padlock probes) [Nilsson et al. 1994, Landegren et al.] for recognition of the target-DNA in combination with enzymatic signal amplification by the RCA mechanism [Fire and Xu, Liu et al.]. The 5' and 3' ends of the linear padlock probe are designed to base-pair next to each other on the target strand. Thereafter, if properly hybridised, the ends can be enzymatically joined by a DNA ligase, thereby creating a circularly closed probe-target complex (reacted probe) for each recognised target. Circularized probes can then be amplified by a DNA polymerase using the RCA mechanism, which generates a DNA strand consisting of a large number of tandem copies of the complement to the circularized probe, collapsing into a random-coil single-stranded DNA macromolecule in solution [Blab et al.]. The RCA process can also be executed by an RNA polymerase creating a corresponding long concatemer RNA strand [Daubendiek and Kool]. Jarvius et al. demonstrated this scheme for DNA single molecule detection. The RCA-products were detected by using fluorescence molecule-tagged probes, designed to hybridise to the repeated sequence of the RCA-product, resulting in a confined cluster of fluorophores [Jarvius et al.]. These clusters were in turn detected and quantified by pumping the sample through a microfluidic device mounted in a standard confocal fluorescence microscope operating in line-scan mode, thereby allowing for digital quantification [ibid]. Furthermore, various circularized probe-target complexes, each corresponding to a unique target sequence, could be formed and amplified simultaneously [ibid]. Hybridization of fluorescence probes with different colours provided the opportunity to perform multiplexed target analysis [ibid]. Although fluorescence detection of the RCA-products, the current state-of-the-art method for DNA sequence detection, has several advantages such as high selectivity and sensitivity, the equipment needed for this is expensive and rather difficult to miniaturize.

Biomolecule detection by measuring changes in the Brownian relaxation frequency of magnetic nanoparticles in aqueous solution was originally proposed by Connolly and St Pierre. In their detection scheme, the surfaces of magnetic nanoparticles are biofunctionalized with probe molecules, e.g. single-stranded oligonucleotide molecules. When single-stranded DNA molecules having a sequence that matches the probe oligonucleotides are added, hybridization reactions occur on the surface of the magnetic nanoparticles, giving rise to an increased hydrodynamic diameter and consequently, a decreased Brownian relaxation frequency. This detection principle has been demonstrated in the case of antigen-antibody reaction by Astalan et al. The complex magnetization spectra were recorded using induction coils and a lock-in amplifier technique. Another example of a magnetic nanoparticle based scheme without fluorescence read-out is the high sensitivity InSb Hall effect biosensor for DNA detection using functionalised magnetic nanoparticles [Togawa et al.] and the giant magnetoresistive biosensor device for magnetic DNA detection [Tamanaha et al.]. Common for the above described magnetic detection schemes are that a rather large number of probe-target hybridization events on the surface of the magnetic nanoparticles are required to produce a reliable output signal.

SUMMARY OF THE INVENTION

The present invention relates to novel detection or quantifying methods for biological entities or molecules such as, but not limited to, DNA, microorganisms and pathogens, proteins and antibodies, that by themselves are target molecules or from which target molecules are extracted. The detection methods are also intended for single molecule detection.

According to a first aspect, the methods comprise the steps of i) forming target molecule-dependent volume-amplified entities, ii) allowing magnetic nanoparticles to bind to said volume-amplified entities, and iii) measuring changes in dynamic magnetic response of the magnetic nanoparticles caused by the increase in hydrodynamic volume of said magnetic nanoparticles or measuring the magnetic field due to the magnetic nanoparticles as they bind to a sensor surface functionalized with a secondary capturing probe.

Said volume-amplified entities may i) comprise the target molecule bound to a particle, which is magnetic or non-magnetic, preferably non-magnetic particle, and functionalised with a secondary capturing molecule (herein and in the following this particle is referred to as a passive particle), or ii) be a Rolling Circle Amplified (RCA) product formed through a target-dependent DNA circularization reaction or iii) comprise such a RCA product bound to such a passive particle.

For the purpose of the invention, a nanoparticle is herein defined as a particle with a radius below 10 µm, preferably below 5 µm, more preferably below 1 µm, most preferably below 500 nm.

In a further embodiment, as mentioned above, the hydrodynamic volume of the target molecule may be directly increased by binding said target molecule to a passive particle via a secondary capturing probe.

The hydrodynamic volume of the entity after amplification should be increased to a size that makes it larger than the biological target to be detected by at least 10%, preferably 20%, more preferably 50%, even more preferably 100%, and most preferably 500%. The great increase in hydrodynamic volume affects the Brownian rotation and the dynamic magnetic properties (complex magnetization) of the magnetic nanoparticle bound to the volume-amplified entity in such a degree that quantification and/or detection step of a biological entity is enabled.

The method according to the present invention has the ability to measure very small quantities of the target, i.e. smaller than 1 nM, preferably smaller than 100 pM, even more preferably smaller than 10 pM. The present invention may therefore be used either to detect the presence of a biological entity or to quantify its concentration in a biological sample. The biological entity may for example be single-stranded DNA, RNA or a protein.

In another embodiment, the biological entity to be quantified and/or detected is a specific protein, protein complexes, or post-translationally modified forms of proteins correlated with different diseases or medical disorders. In such a case, proximity probes may be used in combination with the RCA technique.

As volume-amplified entities bind to functionalized magnetic nanoparticles, the magnitude of the imaginary part of the complex magnetization (or the complex susceptibility or its equivalent) in the vicinity of the Brownian relaxation frequency of the functionalized, and non-reacted, magnetic nanoparticles will significantly diminish. Simultaneously, the magnitude of the imaginary part of the complex magnetization (or the complex susceptibility or its equivalent) in the vicinity of the Brownian relaxation frequency of the magnetic nanoparticles with the volume-amplified entities attached to them will increase, see FIG. 4 and Example 1 for more details. These events give rise to a number of possible ways of detection, some of which are exemplified below.

In another embodiment, the present invention relates to multi-target detection by having several nanoparticle sizes, e.g. one for each target molecule, or several nanoparticles having different capturing probes specific for different target molecules.

Thus, if the RCA-coils are present in a test sample, i.e. if the target-molecule was present originally, the probe-tagged magnetic nanoparticles will be incorporated into the RCA-coils by base-pair hybridization. Upon this, the dynamic magnetic response of the nanoparticles, i.e. the complex magnetization vs. frequency or the magnetization vs. time profile or even the magnetization noise spectrum, changes dramatically. This enables quantification and/or detection.

The detection method according to the present invention, for example implemented as a DNA sequence detection method relying on changes in magnetic properties in combination with the powerful padlock probe and RCA concepts, opens up potential possibilities to design high-sensitivity point-of-care and/or over-the-counter diagnostic tests at a much lower cost compared to already existing ones. It also opens up possibilities to design inexpensive high-sensitivity tests that can detect the presence (qualitative tests) and the concentration (quantitative tests) of microorganisms such as bacteria, viruses, and fungi, for bed-side and point-of-care applications and in veterinary medicine, in e.g. tests for biological contaminations or contents in food and pharmaceutical products, in water, air and environment, in military materials analysis, forensic analysis, etc. Examples of microorganisms that may be detected are, but not limited to, pneumococci, hemophilus, meningococci, tuberculosis and pertussis bacteria, the herpes viruses, candida and aspergillus fungi, plasmodium falciparum (causing malaria), E. coli, influenza, HIV as well as other RNA viruses. In this implementation of the technique, padlock probes are designed to target microbe-specific DNA/RNA sequences such that the padlock probes become circularized in a strictly target-dependent manner upon hybridization and ligation to the targeted DNA/RNA sequence. The formed DNA circles can then be replicated in a strictly circle-dependent RCA reaction, forming long tandem-repeated concatemer DNA molecules [Jarvius et al.]. The technique can be generalized to detection, quantification and analysis of any DNA or RNA sequence, e.g. genotyping of single-nucleotide polymorphisms, quantification of mRNA molecules or gene copy numbers.

A proof of concept for one way of implementing the present invention was published by the present inventors and is hereby incorporated by reference [Strömberg et al. 2008a]. In said scientific paper a fluorophore was used to enable analysis of the number of oligonucleotides on each nanoparticle and to study the samples in a fluorescence microscope. Said fluorescence-labelling was however only used to verify the method.

The present invention further relates to a biosensor for use with the above mentioned method. Said biosensor is a mass-producible, low-cost and sensitive device producing the desired read-out signal, which in one embodiment is designed to be compatible with Fannin's toroidal technique [Fannin et al.]. Such a biosensor in combination with the above-mentioned method represents a fast, cheap and easy-handled way of measuring the complex magnetization of a liquid sample containing nanoparticles.

In a further aspect, the present invention pertains to kits to be used in the above-mentioned method.

Additional embodiments of the invention, along with advantages thereof, will be apparent in view of the following detailed description and examples.

BRIEF DESCRIPTION OF THE DRAWINGS

The following detailed description will be more fully understood in view of the drawing in which.

DETAILED DESCRIPTION

Figure 1:
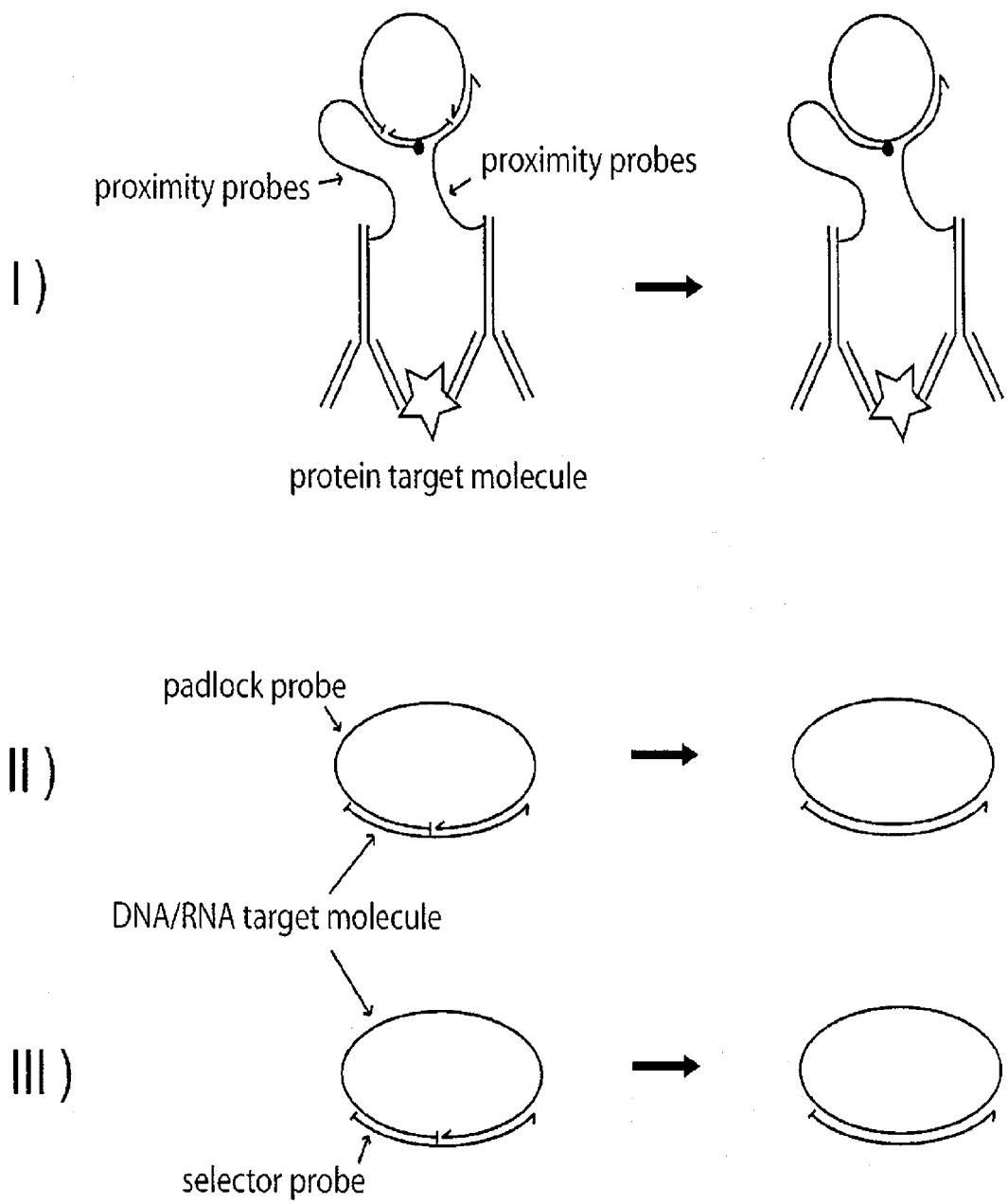
FIG. 1 shows some examples of probing technologies where reacted probes create nucleic acids circles upon specific recognition of target molecules. I) Proximity probes recognize one or more target molecules (in this case the antibodies have recognised and bound to a protein target) and together with accompanying oligonucleotides enable the formation of a nucleic acids circle. A ligase enzyme can then join the ends of the probes and form a closed nucleic acids circle. II) A padlock probe recognizes a specific DNA or RNA target molecule. Correct hybridization between the padlock probe and the DNA or RNA target molecule enables joining of the padlock probe ends, which forms a nucleic acids circle which may be joined by the addition of a ligase enzyme. III) A selector probe recognizes a specific DNA or RNA target molecule. Correct hybridization between the selector probe and the DNA or RNA target molecule enables joining of the DNA or RNA target molecule ends, which forms a nucleic acids circle which may be joined by the addition of a ligase enzyme. The circles produced in I, II and III, may then be amplified by Rolling Circle Amplification (RCA).
Figure 2:
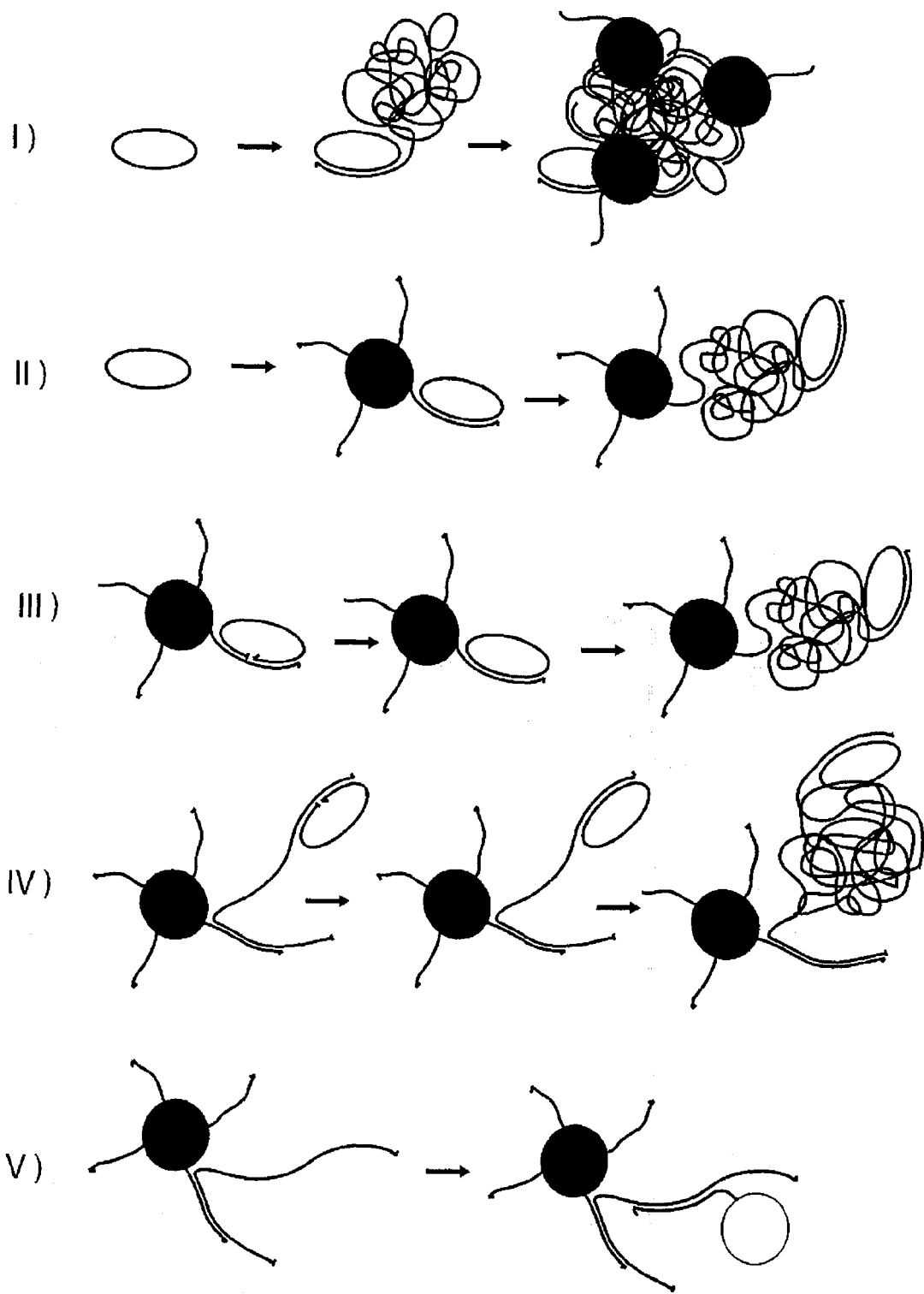
FIG. 2 demonstrates volume-amplification by RCA or hybridization of passive particles functionalized with secondary capturing probes. I) Preformed nucleic acids circles (created as shown in FIG. 1 or by another suitable strategy), are amplified with RCA, and the RCA products are detected with magnetic nanoparticles functionalized with primary capturing probes or according to any of the procedures illustrated in FIG. 3. II) Preformed nucleic acids circles (created as shown in FIG. 1: I-III or by another strategy) are captured with magnetic nanoparticles functionalized with primary capturing probes and amplified with RCA. The RCA products are thereby linked to the magnetic nanoparticles. The RCA products can be detected with additional magnetic nanoparticles functionalized with primary capturing probes or according to any of the procedures illustrated in FIG. 3. III) DNA or RNA target molecules are captured by magnetic nanoparticles functionalized with selector probes. Correct hybridization between the selector probe and the DNA or RNA target molecule enables joining of the DNA or RNA target molecule ends, which forms a nucleic acids circle, which is amplified with RCA. The RCA products are therefore linked to the magnetic nanoparticles. The RCA products can be detected with additional magnetic nanoparticles functionalized with primary capturing probes or according to any of the procedures illustrated in FIG. 3. IV) DNA or RNA target molecules are captured by magnetic nanoparticles functionalized with primary capturing probes and padlock probes are added. Correct hybridization between the padlock probe and the DNA or RNA target molecule enables joining of the padlock probe ends, which forms a nucleic acids circle, which is amplified with RCA. The RCA products are then linked by hybridization with the magnetic nanoparticles. The RCA products can be detected with additional magnetic nanoparticles functionalized with primary capturing probes or according to any of the procedures illustrated in FIG. 3. V) DNA or RNA target molecules are captured by magnetic nanoparticles functionalized with primary capturing probes. Hybridization of passive particles functionalized with secondary capturing probes amplifies the hydrodynamic volume of the magnetic nanoparticles (sandwich type assay).
Figure 3:
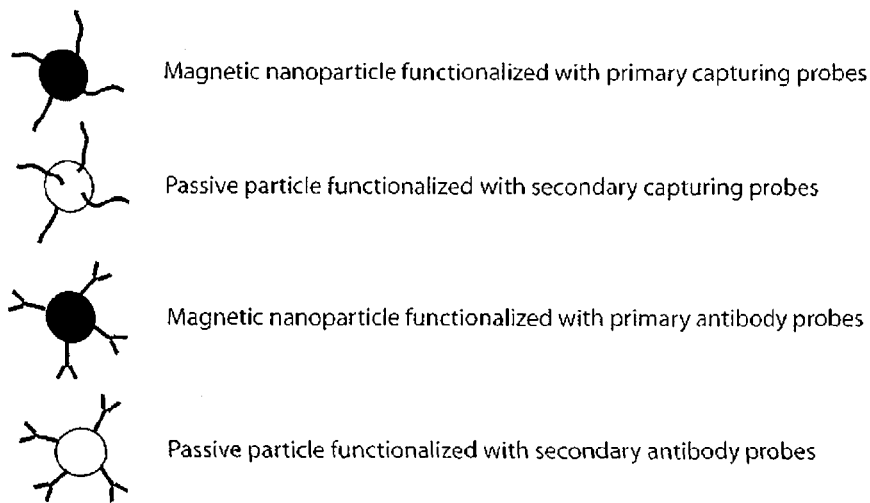
FIG. 3 illustrates examples of strategies for detection of target molecules. RCA products (C) are captured by magnetic nanoparticles functionalized with primary capturing probes (E) with (A) or without (C) passive particles functionalized with secondary capturing probes. A protein target molecule is captured by magnetic nanoparticles functionalized with primary antibody probes (F) and the hydrodynamic volume is increased by binding of passive particles functionalized with secondary antibody probes (D). DNA or RNA target molecules are captured by magnetic nanoparticles functionalized with primary capturing probes (E) and the hydrodynamic volume is increased by hybridization of passive particles functionalized with secondary capturing probes (B). Unbound magnetic nanoparticles functionalized with primary capturing or antibody probes (E and F) are detected as a high-frequency peak in the diagram in G as illustrated in H. Bound magnetic nanoparticles functionalized with primary capturing or antibody probes are detected as a low-frequency peak in the diagram in G as illustrated in H. The magnetic nanoparticle incorporation results in an imaginary part of complex magnetization vs. frequency curve (positive sample, magnetization curve comprising boxes) substantially different from the response of a sample containing free magnetic nanoparticles only, i.e. absence of RCA-products (negative control sample, magnetization curve comprising circles). The two relaxation events in the curve comprising boxes have been resolved (bold black curves) using a Cole-Cole fitting procedure and the peak frequency values are indicated [Strömberg et al. 2008a].
Figure 3:
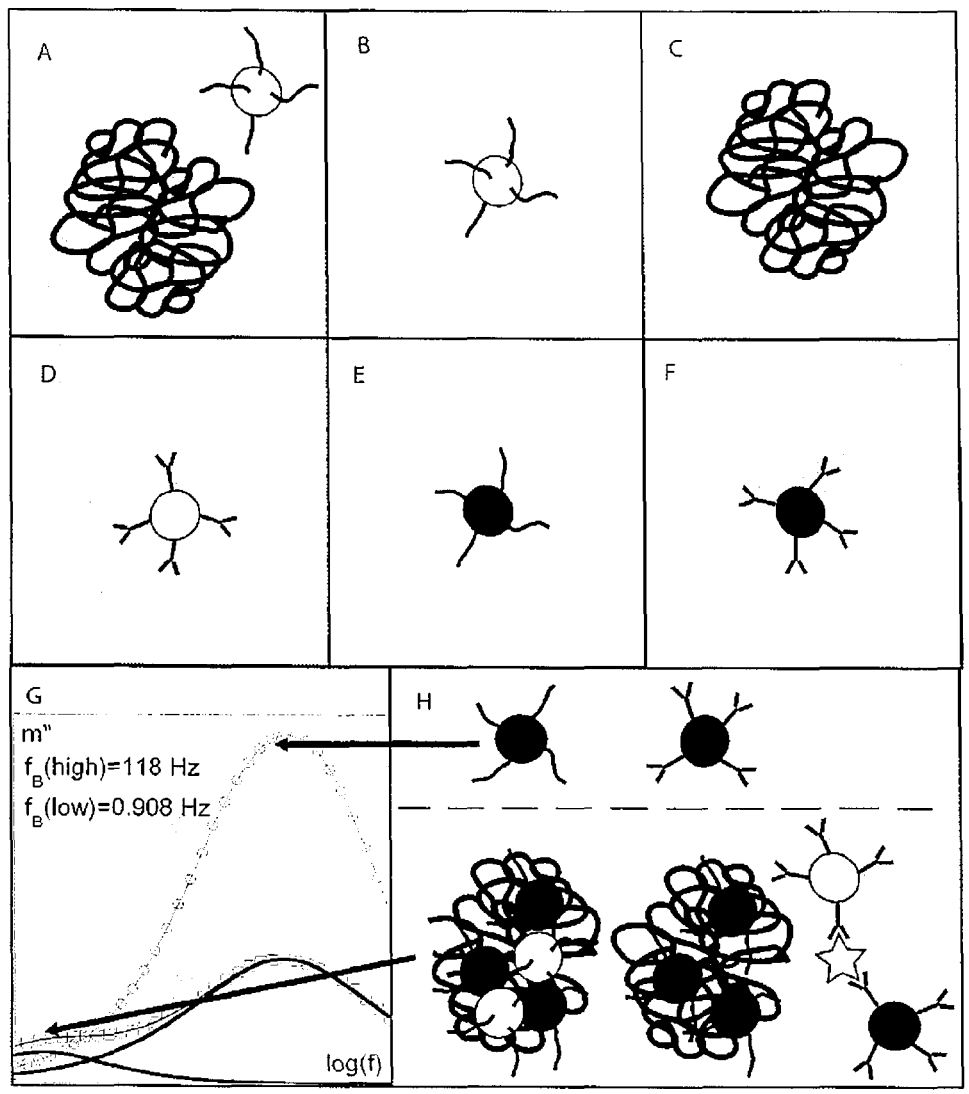

As mentioned above, the present invention relates to a method for quantifying and/or detecting a target molecule, comprising the steps of:

1) forming a target molecule-dependent volume-amplified entity;

2) allowing a magnetic nanoparticle, functionalized with a primary capturing molecule, to bind to said volume-amplified entity via said primary capturing molecule;

3) quantifying and/or detecting the target molecule by measuring the change in dynamic magnetic response of the magnetic nanoparticle caused by the increase in hydrodynamic volume of said magnetic nanoparticle, or measuring the magnetic field due to the magnetic nanoparticle as it binds to a sensor surface functionalized with a secondary capturing probe.

The increase in hydrodynamic volume may be achieved in several ways. The target molecule-dependent volume-amplified entity may comprise a target molecule bound to a passive particle functionalised with a secondary capturing molecule, be a Rolling Circle Amplified (RCA) product formed through a target-dependent DNA circularization reaction, or be a RCA product formed through a target-dependent DNA circularization reaction and bound to a passive particle functionalised with a secondary capturing molecule.

An example of a biological entity that may be detected using the method according to the present invention, is DNA (e.g. a single-stranded nucleic acid sequence) that can form RCA-products upon hybridization and ligation.

The biological entity to be quantified and/or detected may be a specific DNA sequence. The detection method may in such a case comprise adding matching padlock probe molecules to the specific target DNA sequence and allowing said DNA sequences to hybridize and template circularization of the padlock probe. The ends of the padlock probes molecules are then ligated by adding a ligating enzyme. The circularized padlock probes are then amplified by the RCA mechanism, at the addition of DNA polymerases, which results in random-coiled DNA macromolecules (i.e. repeated DNA target sequences) exhibiting repeating DNA sequences of the target molecule. Said random-coiled DNA macromolecules are then allowed to bind to magnetic nanoparticles exhibiting Brownian relaxation behaviour and biofunctionalized with single-stranded oligonucleotide probe molecules (primary capturing probes) containing a sequence complementary to that of the repeating DNA sequence of the random-coiled DNA macromolecules. When mixing the magnetic nanoparticles and the random-coiled DNA macromolecules, the probe-tagged magnetic nanoparticles are incorporated into the RCA-coils by base-pair hybridization between the complementary DNA sequences. Upon this, the dynamic magnetic response of the magnetic nanoparticles, e.g. the complex magnetization vs. frequency profile, changes dramatically, and the DNA target may thus be quantified and/or detected.

Thus, in one embodiment, such a RCA product is formed by:

adding padlock probes having a DNA sequence which is complementary to that of the target molecule;

allowing the ends of the padlock probes to hybridize to said single-stranded nucleic acid sequence and;

ligating the ends of the padlock probes into a circularly closed molecule using a DNA ligase; and amplifying the circular DNA sequence by adding DNA or RNA polymerase and creating random-coiled nucleic acid macromolecules comprising a repeated nucleic acid motif, through the RCA mechanism, to which the magnetic nanoparticles are coupled via the primary capturing molecules on their surface which have a nucleic acid sequence that is complementary to a part of the repeating motif in the nucleic acid macromolecules.

Other biomolecules than DNA which are capable of producing RCA-products may also be used (FIG. 1). A protein molecule may for example be detected as a consequence of coincident binding of two or more specific antibodies equipped with DNA strands, i.e. detection with proximity ligation probes [Fredriksson et al.]. The proximity ligation assay can be configured in such a way that it forms a DNA circle in target-protein dependent manner, which can be amplified using the RCA reaction [Jarvius et al., Söderberg et al., Landegren et al.].

In a further embodiment, the biological entity to be quantified and/or detected is a specific RNA sequence. This can also be accomplished by using padlock probes, as described hereinbefore for the quantification and/or detection of single-stranded DNA [Nilsson et al. 2000].

The biological entity to be quantified and/or detected is a specific protein. In such a case, proximity probes may be used to bind to the target protein. The proximity probes are designed such that their constituent antibodies are specific for the target protein and have affinity for neighbouring parts of the target protein. Each of the antibodies is coupled to a probe DNA sequence, for example an oligonucleotide. When said antibodies are allowed to bind to the target protein, a DNA molecule, which hybridizes to the ends of the probe sequences, is added. Ligation of the probe sequences is then achieved by adding a ligating enzyme. The ligated sequences are after circularization amplified by adding DNA polymerase and creating random-coiled DNA macromolecules (i.e. repeated DNA sequences) through the RCA-mechanism [Jarvius et al.]. Finally, a magnetic nanoparticle is allowed to bind to the DNA macromolecules via a probe molecule that has a DNA sequence that is complementary to that of the DNA macromolecule. Upon this, the dynamic magnetic response of the magnetic nanoparticles, e.g. the complex magnetization vs. frequency profile, changes dramatically, and the protein target may thus be quantified and/or detected.

Thus, in an embodiment suitable for detection of proteins, the RCA product may be formed by:
- adding proximity probes comprising two antibodies being specific for the protein and having affinity for neighbouring parts of the protein, and which antibodies each exhibits a probe DNA sequence;
- allowing said antibodies to bind to the protein;
- adding two DNA molecules that hybridize to the probe DNA sequences forming a nicked structure with both probe DNA sequences;
- circularizing said DNA molecules by adding an enzyme which ligates said nicked structures; and
- and amplifying the ligated DNA by adding DNA or RNA polymerase and creating random-coiled nucleic acid macromolecules comprising a repeated nucleic acid motif, through the RCA mechanism, to which the magnetic nanoparticles are coupled via the primary capturing molecules on their surface which have a nucleic acid sequence that is complementary to a part of the repeating motif in the nucleic acid macromolecules.

In an embodiment of the detection method using RCA-products, the RCA process is allowed to continue during more than 2 seconds, preferably more than 10 seconds, preferably more than 30 seconds, preferably more than 1 minute, even more preferably more than 10 minutes.

The invention also covers multi-target analysis, i.e. several target biomolecules can be simultaneously detected and quantified. If it is desired to detect several single-stranded DNA target molecules simultaneously in a liquid sample, then each target should correspond to one specific padlock probe and if this target is present, RCA-products with a specific repeating sequence are formed. For each kind of RCA-product, one specific primary capturing molecule (e.g. a oligonucleotide) and magnetic nanoparticle size is chosen and the different magnetic nanoparticle sizes with their respective probes attached are mixed together to a multi-sized batch. In the simplest case, if magnetic nanoparticles with very different sizes are selected for said different probes, the imaginary part of magnetization vs. frequency spectrum will exhibit a number of well separated Brownian relaxation peaks. The presence of one target gives a decrease of the corresponding relaxation peak height. However, overlapping free magnetic nanoparticle relaxation peaks is not a problem since the total imaginary part of complex magnetization vs. frequency profile for a multi-target sample can be deconvoluted so that each relaxation peak can be resolved. Using proximity probes, the multi-target detection may also be achieved in case of proteins. This also holds for RNA and so forth. Just mentioned multi-target analysis of DNA was qualitatively demonstrated in [Strömberg et al. 2008b].

The magnetic nanoparticles mentioned herein may be of different kinds, but are normally of matrix or core-shell type. The matrix type magnetic nanoparticle may comprise a porous silica, latex or polymer matrix filled with nanometer-sized magnetic particles. The core-shell type may comprise a core of nanometer-sized magnetic particles, covered with a non-magnetic coating that can be either silica, latex or a polymer. Nanometer-sized in this connection means smaller than 100 nm, preferably smaller than 50 nm but preferably larger than 10 nm. Said nanoparticle may comprise maghemite ($\gamma$-$Fe_2O_3$) or magnetite ($Fe_3O_4$). The magnetic nanoparticles may have a size smaller than 10 µm, preferably smaller than 1 µm, preferably smaller than 300 nm, even more preferably smaller than 270 nm.

The hydrodynamic volume of a target molecule to be detected, may be increased by functionalizing not only magnetic nanoparticles with a molecule that will bind to the target molecule, but also by functionalizing a small passive particle which may be magnetic or non-magnetic, preferably non-magnetic, with such a molecule. Examples of such specific binders or probing molecules are single-stranded oligonucleotide probes (that contain a sequence complementary to a specific part of the biomolecular target, e.g. complementary with the repeating motif in an RCA-coils when these are the products to be detected) for nucleic acids detection, and antibodies for detection of proteins and other macromolecules.

According to one embodiment of the invention, the biological entity to be detected or quantified is allowed to bind to a passive particle which is functionalized to bind to the target molecule. The target molecule and the passive particle, optionally after separation from non-reacted components in the reaction medium, are then allowed to bind to magnetic nanoparticles. This binding can be achieved via groups on the two particles or via interaction between the target molecule and the magnetic nanoparticles. Methods for functionalization of particles with various groups suitable for interaction with other components, are well known in the art and are easily used also in methods according to this invention.

The passive particles, which are used in such sandwich assays, may comprise polystyrene, latex, silver or gold, and be functionalised with a secondary capturing molecule. Examples of such passive particles are, but not limited to, coloured and/or fluorescent or non-labelled particles. Said particle may have a size larger than 1 nm, more preferably larger than 5 nm, but preferably smaller than 10 µm, more preferably smaller than 1 µm.

The primary capturing probe may be selected from DNA, RNA, antibody or fragments thereof. A secondary capturing probe may be selected from DNA, RNA, antibody or fragments thereof.

The method according to the present invention is also suitable for multi-target quantification and/or detection method if employing magnetic nanoparticles of different size or magnetic nanoparticles bound to different molecular probes matching each target, or a combination thereof.

In an alternative embodiment, the quantification and/or detection may be performed directly on a sensor surface. In one embodiment, such a method comprises the steps of:
- immobilizing a secondary capturing molecule on said sensor surface;
- i) allowing said secondary capturing molecule to bind to the target to be detected and forming a capturing molecule-target complex and forming a RCA product from said complex; or
- ii) allowing said secondary capturing molecule to bind a RCA product formed outside the sensor surface;
- allowing the magnetic particle to bind to the RCA product via its primary capturing molecules; and
- measuring the magnetic field caused by the magnetic particle as it binds to the sensor surface.

In addition to detecting the magnitude of the imaginary part of the complex magnetization or its equivalent, e.g. the complex magnetic susceptibility of the reacted magnetic nanoparticles, and comparing it to the corresponding magnitude for non-reacted magnetic nanoparticles at the Brownian relaxation frequency for the non-reacted nanoparticles, a number of other read-out principles may be used to detect the changing dynamic response to the applied magnetic field of the magnetic nanoparticles upon a positive reaction with a target molecule. Such read-out principles include, but are not limited to, comparing the area under the imaginary magnetization (or its equivalent) curve for the reacted magnetic nanoparticles and the non-reacted magnetic nanoparticles in vicinity of the Brownian relaxation peak for the non-reacted magnetic nanoparticles, comparing the magnitude of the imaginary part of the magnetization (or its equivalent) of the reacted magnetic nanoparticles and the non-reacted magnetic nanoparticles at the Brownian relaxation frequency for the reacted magnetic nanoparticles (which is located at a lower frequency than that of the non-reacted magnetic nanoparticles), or comparing the area under the imaginary magnetization (or its equivalent) curve for the reacted magnetic nanoparticles and the non-reacted magnetic nanoparticles in vicinity of the Brownian relaxation peak for the reacted magnetic nanoparticles.

The invention can also be implemented by a read-out device that uses as detection principle the reading of the imaginary and/or the real part of the magnetization (or its equivalent) at a given specific frequency, any Brownian relaxation frequency of the system or another frequency, or the area under the complex magnetization curve in a pre-specified frequency interval. The magnetic response of functionalised magnetic nanoparticles that have been allowed to react with a material (including, but not limited to, liquids, gases and solids) possibly containing a target that positively matches the functionalization of the nanoparticle surface can be compared to the response of a known concentration of non-reacted nanoparticles, but it can also be used alone without comparison to the response of non-reacted nanoparticles.

The present invention further relates to a biosensor for use in the above mentioned method. In one embodiment, such a biosensor for use with the method according to the present invention, is a miniaturized read-out biosensor adapted to operate at ambient temperature and which comprises microfluidics of Fannin's toroidal circuit type, including a ring shaped soft-magnetic core (high magnetic permeability) with a small gap cut at one position and wire windings wound with several turns of a thin conducting wire, and wherein said magnetic circuit produces an oscillating magnetic field in the gap during application of an AC current through the coil windings, and which oscillating magnetic field is suitable for measurement of the frequency dependent complex magnetization of a sample filling the gap of the toroidal circuit. Said biosensor may be used for rapid detection, and may for example be used for home tests.

The above example serves to illustrate one possible miniaturized read-out biosensor which may provide a mass-producible low-cost and sensitive device to get the desired read-out signal. A fast, cheap and easy-handled method to measure the complex magnetization of a liquid sample containing nanoparticles is the so-called Fannin's toroidal technique [Fannin et al.]. This device (dimensions of several cm) is constituted by a circular ring shaped soft-magnetic core (high magnetic permeability) with a small gap cut at one position. The wire windings of the toroid are wound with several turns of a thin conducting wire. An ac current is applied through the wire which creates an oscillating magnetic field in the gap. By measuring the complex impedance of the circuit during a frequency sweep with the gap filled by sample and empty gap, the complex magnetization for the nanoparticle sample can be obtained (for instance a sample of RCA-products with incorporated nanoparticles). Also, miniaturized Hall-sensors [Togawa et al.] constitute a potential candidate for a miniaturized read-out biosensor.

In one embodiment, the present invention relates to a biosensor like the one above-described, but with dimensions of some hundreds of micrometers or even smaller. Miniaturizing will strongly increase measurement sensitivity and thereby reduce sample volumes, etc. The sample is suitably inserted to or removed from the gap by letting a microfluidic channel pass through the gap.

The reading of the dynamic magnetic response of nanoparticles, which have been in contact with a material possibly containing a positive target and which hydrodynamic volume has been enlarged or amplified, can also be measured in the time domain as an alternative to frequency domain read-out. Such reading principles can be based on, but are not limited to, detection of the time dependent magnetization of the nanoparticles following a step-change in applied magnetic field using miniaturised magnetoresistive sensors [Tamanaha et al.]. The lateral size of such a sensor could be smaller than 10 mm, preferably smaller than 1 mm, preferably smaller than 0.1 mm, preferably smaller than 30 µm, even more preferably smaller than 10 µm.

The detection can also be based on reading the magnetization noise of the nanoparticles, which can be either equilibrium magnetization noise, in which case there exists a fluctuation-dissipation theorem relating the measured noise to the imaginary part of the magnetization, or non-equilibrium magnetization noise created by trapping/detrapping of magnetic nanoparticles by RCA-products. The magnetization noise can be measured in zero-field or after having applied a step-change in magnetic field. The detection principle can be based on, but are not limited to, a miniaturised magnetoresistive sensor as described above.

The present invention also relates to kits for use in the above mentioned method. In one embodiment, said kit for use with the method according to the present invention, comprises padlock probes being specific for different DNA or RNA sequences correlated with diseases or medical disorders, DNA/RNA ligase to enable probe circularization, DNA/RNA polymerase to enable the forming of RCA products, magnetic nanoparticles equipped with a primary capturing molecule (e.g. an oligonucleotide) having a high specificity for binding to the RCA products, and a lab-on-chip including microfluidics integrated with a miniaturized read-out biosensor device.

In another embodiment, said kit comprises proximity probes being specific for proteins, protein complexes, or post-translationally modified forms of proteins correlated with different diseases or medical disorders, DNA ligase to enable probe circularization, DNA polymerase to enable the forming of RCA products, magnetic nanoparticles equipped with a primary capturing molecule (e.g. an oligonucleotide) having a high specificity for binding to the RCA products, and a lab-on-a-chip including microfluidics integrated with a miniaturized read-out biosensor device.

EXAMPLES

Example 1

Detection of Single-Stranded DNA Using the RCA Technique

Figure 4:
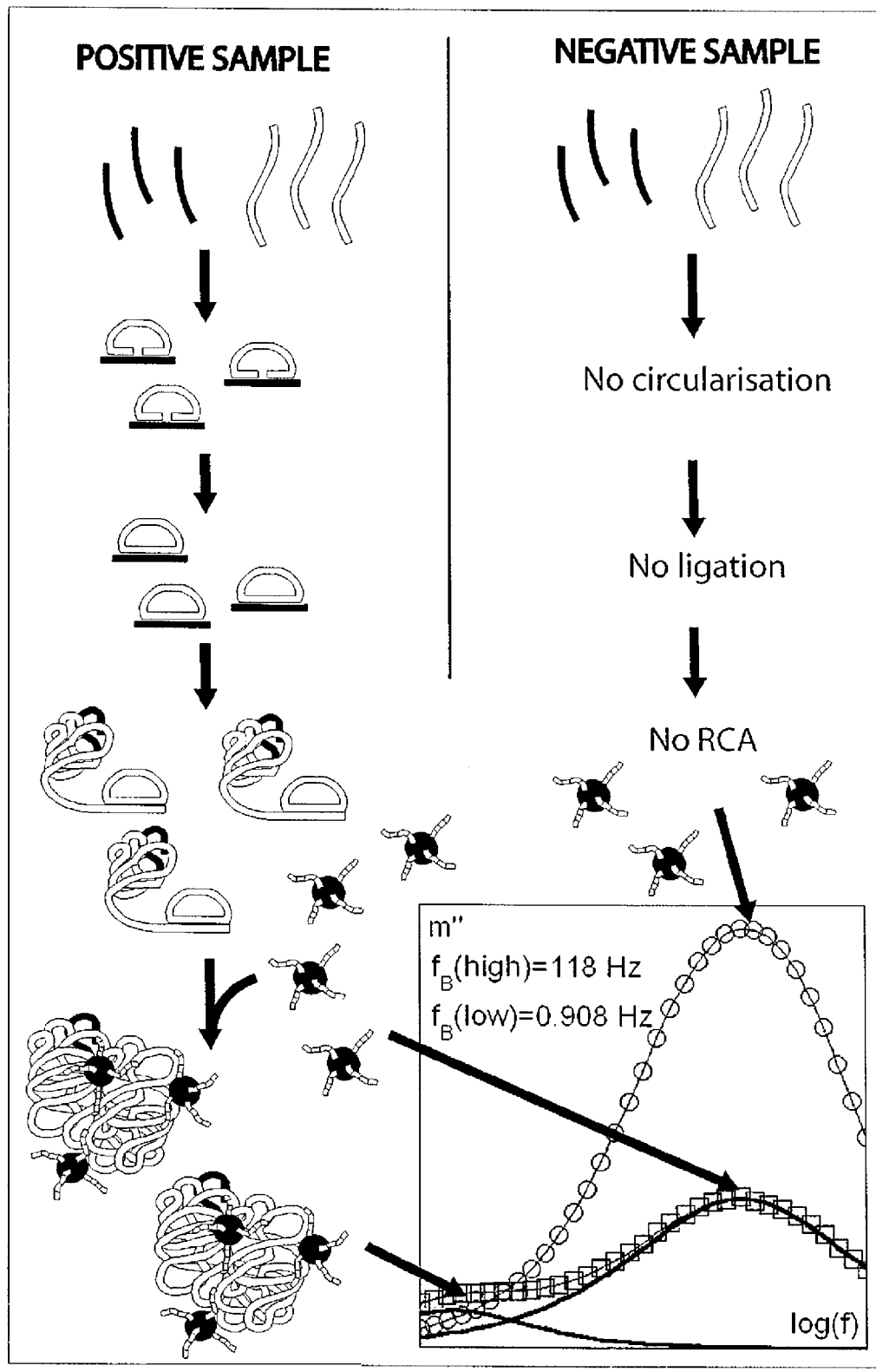
FIG. 4 shows a schematic illustration of the detection method according to the present invention involving the detection of a DNA target: A collection of single-stranded target-DNA molecules (curved black lines) is shown in the upper left part of the figure. After addition of padlock probes matching the target (curved white lines), circularized padlock probes form upon hybridization and the ends of the padlock probe molecules are joined together by ligation. The circularized padlock probes are then amplified through the RCA-mechanism by creating random-coiled DNA macromolecules (RCA-coils or equivalent RCA-products). In order to detect the presence of RCA-products, single-stranded oligonucleotide functionalised magnetic nanoparticles (solid black spheres with curved lines on surface) are added, which are incorporated by base-pair hybridization in the RCA-coils, i.e. the single-stranded oligonucleotides have a sequence complementary to a part of the repeating motif in the RCA-products. The RCA-coil repeating motif equals the complement of the circularized padlock probe. The magnetic nanoparticle incorporation results in a spectrum of the imaginary part of complex magnetization vs. frequency (positive sample, magnetization curve comprising boxes) substantially different from the response of a sample containing free magnetic nanoparticles only, i.e. absence of RCA-products (negative control sample, magnetization curve comprising circles). The two relaxation events in the curve comprising boxes have been resolved (bold black curves) using a Cole-Cole fitting procedure and the peak frequency values are indicated. [Strömberg et al. 2008a].

FIG. 4 shows an example of the invention implemented as single target DNA sequence detection step by step, using the RCA technique for amplification purposes. In upper left part of the figure, a solution containing single-stranded target-DNA molecules, indicated as curved black lines, is shown. Linear padlock probe molecules (curved white lines) designed to exactly match the target-DNA are added, which upon hybridization with the target-DNA molecules form circularized padlock probes. The ends of the padlock probe molecules are joined together by ligation. DNA polymerases are added and the RCA of the circularized padlock probes proceeds for a certain time (the RCA-time). After completion of RCA, the solution comprises random-coil single-stranded molecules having an approximate size of 1 µm (for an RCA-time of approximately 1 hr) [Strömberg et al. 2008a].

The presence of the RCA-coils is detected by addition of magnetic nanoparticles exhibiting Brownian relaxation behaviour biofunctionalized with single-stranded oligonucleotides (total hydrodynamic diameter approximately 150 nm), where the oligonucleotides on surface of the magnetic nanoparticles have a sequence complementary to a part of the repeating motif in the RCA-coils. The magnetic nanoparticles comprise a maghemite ($\gamma$-$Fe_2O_3$) core embedded in a dextran casing and with primary amine groups on the surface where the amine groups serve as oligonucleotide coupling sites. For more details about the nanoparticles and their dynamic magnetic properties, reference is made to [Strömberg et al. 2007b].

The probe-tagged magnetic nanoparticles and the RCA-coils will, during their diffusive motion, approach each other and the probe-tagged magnetic nanoparticles can then be incorporated into the coils by base-pair hybridization. The hydrodynamic size of the incorporated magnetic nanoparticles is strongly altered, such that their diameter essentially corresponds to that of the RCA-coil. Magnetic nanoparticles that are not incorporated exhibit an unaltered hydrodynamic diameter. In case of a negative sample, i.e. when the target-DNA is not present (right part of FIG. 4), no circularized padlock probes and hence no RCA-products are formed. Thus, in this case, all probe-tagged magnetic nanoparticles remain free in solution.

The lower right part of FIG. 4 shows the spectrum for the imaginary part of the frequency-dependent complex magnetization for one positive sample (curve comprising boxes, in this case there is three times as many coils as probe-tagged magnetic nanoparticles) and for a negative control sample (curve comprising circles). The negative control sample exhibits a well defined Brownian relaxation frequency, $f_B$, defined by the frequency at which the imaginary part of the magnetization, m"(f), exhibits a maximum (see [Strömberg et al. 2007a and 2007b] for details on Brownian relaxation frequencies and magnetization), and the peak height gives a measure of the number of free probe-tagged magnetic nanoparticles. The positive sample has essentially two relaxation frequencies where the low-frequency peak mainly corresponds to single RCA-coils with incorporated magnetic nanoparticles and the high-frequency peak arises from probe-tagged magnetic nanoparticles that are still free.

The two relaxation events have been resolved using the Cole-Cole fitting procedure (see [Strömberg et al. 2007a and 2007b]) and the bold black curves show the two contributions to the curve comprising boxes. The extracted peak frequency values are also indicated. By measuring the m" high frequency peak level, it is possible to discriminate between positive and negative samples and, as described below, a target DNA concentration determination can be performed. This example is taken from and experimentally demonstrated in [Strömberg et al. 2008a].

Example 2

Quantification of Single-Stranded DNA Using the RCA Technique (Amplification Before Binding to Magnetic Nanoparticles)

Figure 5:
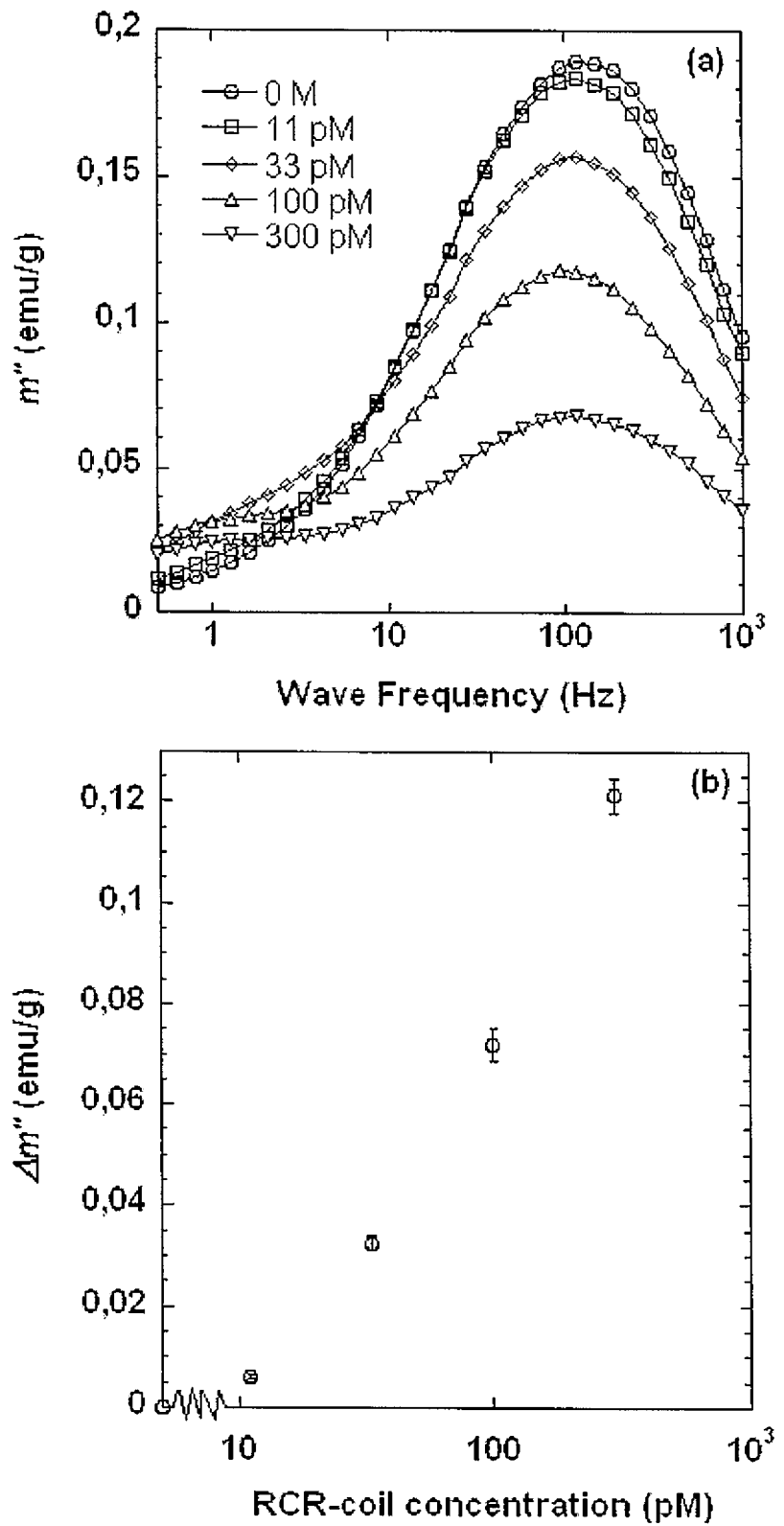
FIG. 5 shows complex magnetization data for different RCA-coil concentrations: (a) Imaginary part of the complex magnetization vs. frequency measured at 310 K for a series of positive samples having RCA-coil concentrations ranging from 0 to 300 pM (probe-tagged magnetic nanoparticle concentration 1 nM, RCA-time 1 hr, the sample preparation was incubated for 30 min at 343 K). The "0 M" curve corresponds to a negative control sample. (b) shows $\Delta m''=m''(0)-m''(c)$ at the high frequency peak vs. RCA-coil concentration c with error bars included. Note the excellent reproducibility. [Strömberg et al. 2008a].

FIG. 5 (*a*) shows the imaginary part of the complex magnetization vs. frequency at 310 K for positive samples with various RCA-coil concentrations, ranging from 0 to 300 pM. The magnetic properties of the synthesised probe-tagged magnetic nanoparticles were found to be highly reproducible. The "0 M" curve corresponds to the negative control sample without RCA-coils [Strömberg et al. 2008a].

FIG. 5 (*b*) shows $\Delta$m", defined as $\Delta$m"=m"(0)−m"(c), at the high frequency Brownian relaxation peak vs. RCA-coil concentration, c. Note the very clear correspondence between the high frequency peak m" level and the RCA-product concentration. As the RCA-product concentration increases, more probe-tagged magnetic nanoparticles are incorporated into coils and therefore, the high frequency peak m" level decreases [Strömberg et al. 2008a].

The high and low frequency Brownian relaxation peaks correspond to the expected hydrodynamic sizes of free magnetic nanoparticles and magnetic nanoparticles incorporated into RCA-coils, respectively [Strömberg et al. 2008a]. This is also supported by the fact that the low frequency peak is shifted to higher frequencies when decreasing the RCA-time, i.e. coils with smaller diameter are obtained [ibid]. Furthermore, it has been shown that the changes in the complex magnetization spectrum are solely due to magnetic nanoparticle incorporation by hybridization, by measuring on a negative control sample containing RCA-coils having a sequence that is non-complementary to the oligonucleotide probes on the magnetic nanoparticles [ibid].

It has also been shown that the magnetic nanoparticle incorporation speed increases with increasing incubation temperature (up to ~343 K), which is reasonable since the magnetic nanoparticle incorporation is diffusion-controlled [ibid]. It can be concluded from FIG. 5 that a positive sample can be discriminated from a negative control sample at least at the 10 pM level. This limit of detection level compares very favourably with fluorescence polarization measurements of the same RCA-products, where a limit of detection of 100 pM was achieved.

A general remark should be made here: in the current example, the RCA-coil and probe-tagged magnetic nanoparticle concentrations investigated were chosen in order to make magnetic read-out possible using a commercial SQUID magnetometer, with comparably low pick-up coil filling factor. By constructing a miniaturised magnetic circuit, including microfluidics for sample injection, and by using smaller magnetic nanoparticles to increase the Brownian relaxation frequency for free magnetic nanoparticles, it will be possible to increase the measurement sensitivity, thereby allowing for smaller concentrations of RCA-coils and probe-tagged magnetic nanoparticles; in the ideal case single probe-tagged magnetic nanoparticles/RCA-coil complex detection. The RCA-time, magnetic nanoparticle size and magnetic nanoparticle surface coverage of oligonucleotides are other factors that may be optimised to further improve the level of detection. These parameters have recently been under investigation in [Strömberg et al. 2008b]. For materials properties of nanoparticles related to the current example reference is made to [Strömberg et al. 2007a].

In the current example from [Strömberg et al. 2008a], when magnetic nanoparticles with a bare physical diameter of 130 nm were used, quantitative DNA-target analysis relied on the decrease of the free magnetic nanoparticle relaxation peak height (m" HFP level) with increasing RCA-product concentration. We denote this detection principle turn-off detection. However, the height of the low-frequency peak (m" LFP level) showed no correlation with the RCA-product concentration. In [Strömberg et al. 2008b] the same type of experiment as in FIG. 5 was made using magnetic nanoparticles having a bare physical diameter of 40 nm. In this case, besides the turn-off detection possibility, there was a clear correlation between the m" LFP level and RCA-product concentration, i.e. the m" LFP level increased with increasing RCA-coil concentration. This detection principle we denote turn-on detection—a principle which could be attractive for future biosensor development.

Example 3

Quantification of Single-Stranded DNA Using the RCA Technique (Amplification after Binding to Magnetic Nanoparticles In the above examples the hydrodynamic volume of the target molecule to be detected was enlarged before the binding reaction to functionalized magnetic nanoparticles exhibiting Brownian relaxation behavior. In another implementation of the present invention the hydrodynamic volume of the target molecule that binds to the magnetic nanoparticle is increased after such a binding reaction and prior to read-out.

To exemplify this, thiol modified oligonucleotide probes were immobilized on aminated 130 nm-sized magnetic nanoparticles using SPDP coupling chemistry [Strömberg et al. 2007b, Strömberg et al. 2008a] composed of a non-magnetic dextrane shell enclosing a magnetic aggregate consisting of 15 nm maghemite ($\gamma$-$Fe_2O_3$) nanoparticles, with each nanoparticle being in a single domain state. The types of probes and nanoparticles may however vary depending on desired application.

After a positive reaction between the probes on the magnetic nanoparticle surface and the target sequence had taken place, the padlock probe assay was configured such that the RCA-reaction generated long, concatemeric strands that remain linked to the magnetic nanoparticles and thereby increased the hydrodynamic volume of the magnetic nanoparticles more than the actual hybridization reaction would have done. This is achieved by using the immobilized oligonucleotide as primer for the RCA reaction.

Example 4

Read-Out Format Based on Immobilizing RCA-Products on a Magnetic Sensor Surface

Figure 6:
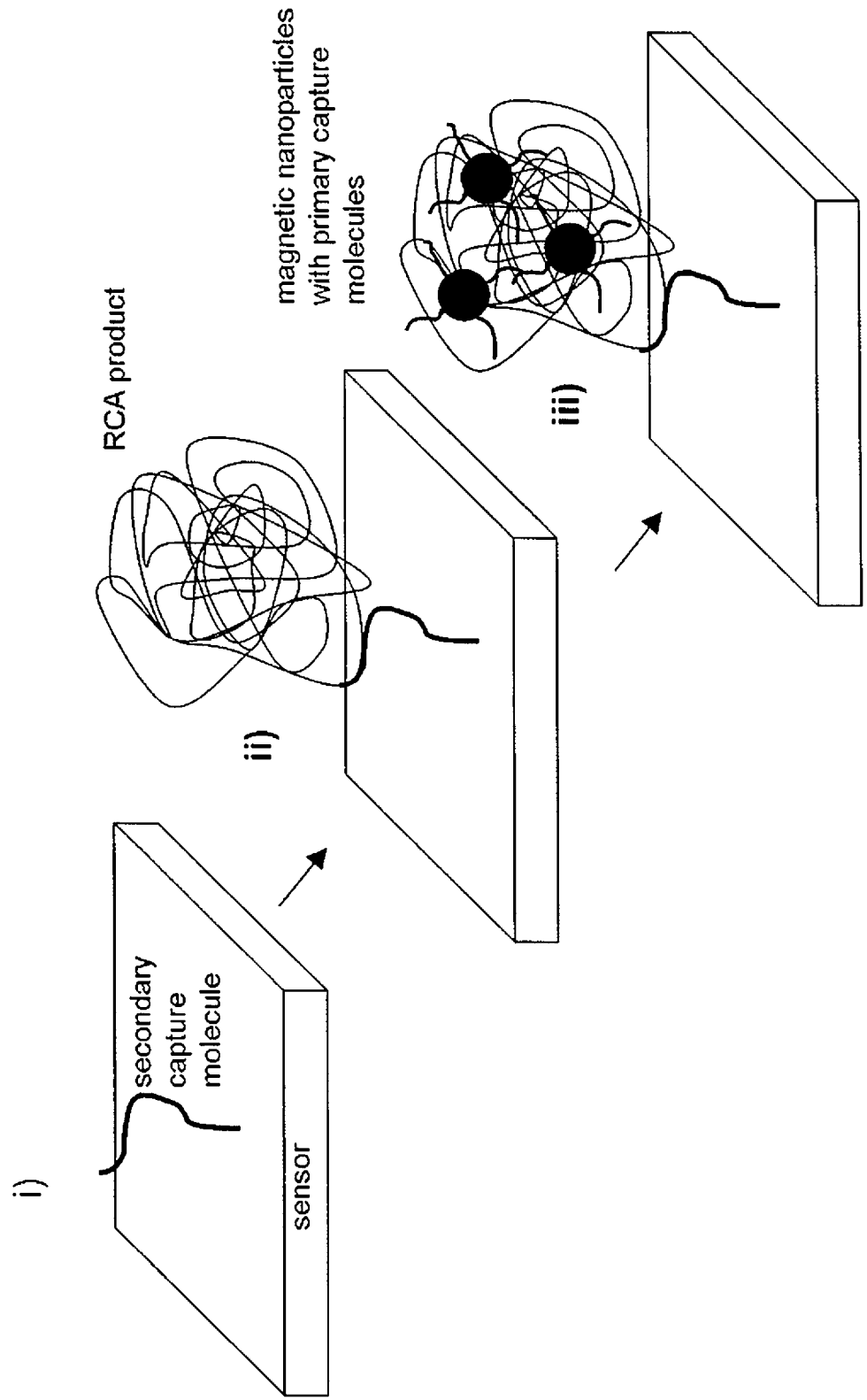
FIG. 6 shows the steps involved when quantifying and/or detecting a target molecule by measuring the magnetic field caused by a magnetic particle as it binds to a sensor surface, through surface-immobilized RCA products. i) The magnetic field sensor surface is functionalized with a secondary capturing molecule that ii) captures an RCA product. iii) The magnetic field detected by the sensor increases as magnetic nanoparticles functionalized with primary capturing molecules bind to the RCA product.

In this example, illustrated in FIG. 6, the surface of a substrate-based magnetic sensor, capable of sensing the magnetic moments of magnetic nanoparticles in close vicinity of the surface, is functionalized with secondary capturing molecules with affinity for a certain type of RCA-product. Magnetic nanoparticles functionalized with primary capturing molecules in order to have affinity for said RCA-products are added. This results in trapping of magnetic nanoparticles in close vicinity of the sensor surface if there are RCA-products present. The sensor surface is thereafter washed in order to remove non-trapped nanoparticles.

The above-mentioned detailed description, examples and appended drawings, show the best currently contemplated modes of carrying out the invention. These are not to be taken in a limiting sense, but are presented for the purpose of illustrating the general principles of the invention and the best mode for practicing the invention.

References

Astalan, A. P.; Ahrentorp, F.; Johansson, C.; Larsson, K.; Krozer, A. *Biosensors and Bioelectronics* 2003, 19, 945-951.

Bally, M.; Halter, M.; Vörös, J.; Grandin, H. M. *Surface and Interface Analysis* 2006, 38, 1442-1458.

Blab, G. A.; Schmidt, T.; Nilsson, M. *Analytical Chemistry* 2004, 76, 495-498.

Connolly, J.; St Pierre, T. G. *Journal of Magnetism and Magnetic Materials* 2001, 225, 156-160.

Daubendiek, S. L.; Kool, E. T. *Nature Biotechnology* 1997, 15, 273-277.

Fannin, P. C.; Scaife, B. K. P.; Charles, S. W. *J. Phys. E: Sci. Instrum.* 1986, 19, 238-239.

Fire, A.; Xu, S.-Q. *Proceedings of the National Academy of Sciences of U.S.A.* 1995, 92, 4641-4645.

Fredriksson, S.; Gullberg, M.; Jarvius, J.; Olsson, C.; Pietras, K.; Gústafsdóttir, S. M.; Östman, A.; Landegren, U. *Nature Biotechnology* 2002, 20, 473-477.

Jarvius, J.; Melin, J.; Göransson, J.; Stenberg, J.; Fredriksson, S.; Gonzalez-Rey, C.; Bertilsson, S.; Nilsson, M. *Nature Methods* 2006, 3, 725-727.

Kerman, K.; Kobayashi, M.; Tamiya, E. *Measurement Science and Technology* 2004, 15, R1-R11.

Landegren, U.; Dahl, F.; Nilsson, M.; Fredriksson, S.; Banér, J.; Gullberg, M.; Jarvius, J.; Gustafsdottir, S.; Söderberg, O.; Ericsson, O.; Stenberg, J.; Schallmeiner, E. *Comparative and Functional Genomics* 2003, 4, 525-530.

Liu, D.; Daubendiek, S. L.; Zillman, M. A.; Ryan, K.; Kool, E. T. *Journal of the American Chemical Society* 1996, 118, 1587-1594.

Nam, J.-M.; Thaxton, C. S.; Mirkin, C. A. *Science* 2003, 301, 1884-1886.

Nilsson, M.; Malmgren, H.; Samiotaki, M.; Kwiatkowski, M.; Chowdhary, B. P.; Landegren, U. *Science* 1994, 265, 2085-2088.

Nilsson, M.; Barbany, G.; Antson, D.-O.; Gertow, K.; Landegren, U. *Nature Biotechnology* 2000, 18, 791-793.

Saiki, R. K.; Scharf, S.; Faloona, F.; Mullis, K. B.; Horn, G. T.; Erlich, H. A.;. Arnheim, N. *Science* 1985, 230, 1350-1354.

Sano, T.; Smith, C. L.; Cantor, C. R. *Science* 1992, 258, 120-122.

Schweitzer, B.; Wiltshire, S.; Lambert, J.; O'Malley, S.; Kukanskis, K.; Zhu, Z.; Kingsmore, S. F.; Lizardi, P. M.; Ward, D. C. *Proceedings of the National Academy of Sciences of U.S.A.* 2000, 97, 10113-10119.

Strömberg, M.; Gunnarsson, K.; Valizadeh, S.; Svedlindh, P.; Strømme, M. *J. Appl. Phys.* 2007a, 101, 023911.

Strömberg, M.; Gunnarsson, K.; Johansson, H.; Nilsson, M.; Svedlindh, P.; Strømme, M. *Journal of Physics D: Applied Physics* 2007b, 40, 1320-1330.

Strömberg, M.; Göransson, J.; Gunnarsson, K.; Nilsson, M.; Svedlindh, P.; Strømme, M. *Nano Letters* 2008a, 8, 816-821.

Strömberg, M.; Zardán Gómez de la Torre, T.; Göransson, J.; Gunnarsson, K.; Nilsson, M.; Strømme, M.; Svedlindh, P. *Biosensors and Bioelectronics* 2008b, doi:10.1016/j.bios.2008.06.043.

Su, M.; Li, S.; Dravid, V. P. *Applied Physics Letters* 2003, 82, 3562-3564.

Söderberg, O.; Gullberg, M.; Jarvius, M.; Ridderstråle, K.; Leuchowius, K.-J.; Jarvius, J.; Wester, K.; Hydbring, P.; Bahram, F.; Larsson, L.-G.; Landegren, U. *Nature Methods* 2006, 3, 995-1000.

Tamanaha, C. R.; Colton, R. J.; Miller, M. M.; Piani, M. A.; Rife, J. C.; Sheehan, P. E.; Whitman, L. J. *Micro Total Analysis Systems* 2001, 444-446, edited by Ramsey, J. M.; van den Berg, A.

Togawa, K.; Sanbonsugi, H.; Sandhu, A.; Abe, M.; Narimatsu, H.; Nishio, K.; Handa, H. *Japanese Journal of Applied Physics* 2005, 44, L1494-L1497.

What is claimed is:

1. A method for quantifying and/or detecting a target molecule, comprising the steps of:
    forming a target molecule-dependent volume-amplified entity comprising i) a target molecule bound to a passive particle functionalized with a secondary capturing molecule, ii) a Rolling Circle Amplified (RCA) product formed through a target-dependent DNA circularization reaction, or iii) a RCA product formed through a target-dependent DNA circularization reaction and bound to a passive particle functionalized with a secondary capturing molecule;
    allowing a magnetic nanoparticle, functionalized with a primary capturing molecule, to bind said volume-amplified entity via said primary capturing molecule; and
    quantifying and/or detecting the target by measuring the change in dynamic magnetic response of the magnetic nanoparticle caused by the increase in hydrodynamic volume of said magnetic nanoparticle, wherein the increase in hydrodynamic volume of the magnetic nanoparticle results from binding with the volume-amplified entity.

2. The method according to claim 1, wherein the target molecule-dependent volume-amplified entity comprises ii) a Rolling Circle Amplified (RCA) product formed through a target-dependent DNA circularization reaction, or iii) a RCA product formed through a target-dependent DNA circularization reaction and bound to a passive particle functionalized with a secondary capturing molecule.

3. The method according to claim 1, wherein the target molecule is a single-stranded nucleic acid sequence.

4. The method according to claim 3, wherein the RCA product is formed by:
    adding padlock probes having a DNA sequence which is complementary to that of the target molecule;
    allowing the ends of the padlock probes to hybridize to said single-stranded nucleic acid sequence;
    ligating the ends of the padlock probes into a circularly closed molecule using a DNA ligase; and
    amplifying the circular DNA sequence by adding DNA or RNA polymerase and creating random-coiled nucleic acid macromolecules comprising a repeated nucleic acid motif, through the RCA mechanism, to which the magnetic nanoparticles are coupled via the primary capturing molecules on their surface which have a nucleic acid sequence that is complementary to a part of the repeating motif in the nucleic acid macromolecules.

5. The method according to claim 1, wherein the target molecule is a protein.

6. The method according to claim 5, wherein the RCA product is formed by:
    adding proximity probes comprising two antibodies being specific for the protein and having affinity for neighbouring parts of the protein, and which antibodies each exhibits a probe DNA sequence;
    allowing said antibodies to bind to the protein;
    adding two DNA molecules that hybridize to the probe DNA sequences forming a nicked structure with both probe DNA sequences;
    circularizing said DNA molecules by adding an enzyme which ligates said nicked structures; and
    amplifying the ligated DNA by adding DNA or RNA polymerase and creating random-coiled nucleic acid macromolecules comprising a repeated nucleic acid motif, through the RCA mechanism, to which the magnetic nanoparticles are coupled via the primary capturing molecules on their surface which have a nucleic acid sequence that is complementary to a part of the repeating motif in the nucleic acid macromolecules.

7. The method according to claim 1, wherein the magnetic nanoparticle is of matrix type.

8. The method according to claim 7, wherein the matrix type magnetic nanoparticle comprises a porous silica, latex or polymer matrix filled with nanometer-sized magnetic particles.

9. The method according to claim 1, wherein the magnetic nanoparticle is of core-shell type.

10. The method according to claim 9, wherein the core-shell type magnetic nanoparticle comprises a core of nanometer-sized magnetic particles, covered with a non-magnetic coating.

11. The method according to claim 10, wherein the non-magnetic coating comprises silica, latex or a polymer or a combination thereof.

12. The method according to claim 1, wherein the magnetic nanoparticle comprises maghemite ($\gamma$-$Fe_2O_3$) or magnetite ($Fe_3O_4$).

13. The method according to claim 1, wherein the passive particle comprises polystyrene, latex, silver or gold.

14. The method according to claim 13, wherein the passive particle has a size larger than 1 nm and smaller than 10 µm.

15. The method according to claim 1, wherein the magnetic nanoparticle has a size larger than 10 nm and smaller than 10 µm.

16. The method according to claim 1, wherein the hydrodynamic volume of the volume-amplified entity is 10% to 500% larger than the volume of the target molecule.

17. The method according to claim 1, wherein the method is a multi-target quantification and/or detection method and employs magnetic nanoparticles of different size or magnetic nanoparticles bound to different molecular probes matching each target, or a combination thereof.

18. The method according to claim 1, wherein the magnetic nanoparticle has a size larger than 10 nm and smaller than 1 µm.

19. The method according to claim 18, wherein the magnetic nanoparticle comprises maghemite ($\gamma$-$Fe_2O_3$) or magnetite ($Fe_3O_4$).

20. The method according to claim 1, wherein the magnetic nanoparticle has a size larger than 10 nm and smaller than 300 nm.

21. The method according to claim 20, wherein the magnetic nanoparticle comprises maghemite ($\gamma$-$Fe_2O_3$) or magnetite ($Fe_3O_4$).

* * * * *